US010639217B2

(12) United States Patent
Merry Del Val (10) Patent No.: US 10,639,217 B2
(45) Date of Patent: May 5, 2020

(54) STERILISING AUTOMATIC DISPENSER OF DISPOSABLE DEVICES FOR AID OF FEMALE URINATION IN A STANDING-UP POSITION

(71) Applicant: SANIPLAST S.R.L., Milan (IT)

(72) Inventor: Domingo Merry Del Val, Montorfano (IT)

(73) Assignee: SANIPLAST S.R.L., Milan (IT)

( * ) Notice: Subject to any disclaimer, the term of this patent is extended or adjusted under 35 U.S.C. 154(b) by 1 day.

(21) Appl. No.: 15/887,587

(22) Filed: Feb. 2, 2018

(65) Prior Publication Data
US 2019/0240089 A1    Aug. 8, 2019

(51) Int. Cl.
| | | |
|---|---|---|
| *A61F 15/00* | (2006.01) | |
| *A61F 5/455* | (2006.01) | |
| *B65D 83/08* | (2006.01) | |
| *A61L 2/10* | (2006.01) | |
| *G07F 11/00* | (2006.01) | |

(52) U.S. Cl.
CPC .......... *A61F 15/001* (2013.01); *A61F 5/4556* (2013.01); *A61L 2/10* (2013.01); *B65D 83/0829* (2013.01); *A61L 2202/24* (2013.01); *G07F 11/00* (2013.01)

(58) Field of Classification Search
CPC ... A47K 10/424; A47K 10/425; A61F 5/4556; A61F 15/001; A61L 2/10; A61L 2202/24; B65D 83/0829; G07F 11/00; G07F 11/005; G07F 11/04; G07F 11/045; G07F 11/62
See application file for complete search history.

(56) References Cited

U.S. PATENT DOCUMENTS

| | | | | |
|---|---|---|---|---|
| 1,460,123 | A * | 6/1923 | Walls ....................... | G07F 13/10 194/294 |
| 4,937,890 | A * | 7/1990 | Tafur ....................... | A47K 11/12 4/144.1 |
| 5,232,123 | A * | 8/1993 | Richardson ............. | G07F 11/22 221/155 |
| 5,301,834 | A * | 4/1994 | Lee ........................ | B65H 3/523 221/129 |
| 5,335,822 | A | 8/1994 | Kasper | |

(Continued)

FOREIGN PATENT DOCUMENTS

| | | |
|---|---|---|
| DE | 21 2006 000067 U1 | 7/2008 |
| EP | D 594 253 A1 | 4/1994 |
| WO | 93/11691 A1 | 6/1993 |

OTHER PUBLICATIONS

IT Search Report, dated Apr. 7, 2016, from IT application No. ITUB20152979.

(Continued)

*Primary Examiner* — Gene O Crawford
*Assistant Examiner* — Kelvin L Randall, Jr.
(74) *Attorney, Agent, or Firm* — Young & Thompson (57) ABSTRACT

A description is given of a sterilising automatic dispenser apt to dispense flattened disposable devices as an aid to female urination in standing position provided with a curved portion, wherein the forward movement unit is apt to make the FUD move forwards in the outlet slot by direct pushing on the indentation of the FUD or by way of contact with friction of the FUD with the forward movement unit.

21 Claims, 7 Drawing Sheets

(56) References Cited

U.S. PATENT DOCUMENTS

| | | | |
|---|---|---|---|
| 5,611,456 A * | 3/1997 | Kasper | B65H 1/06 221/129 |
| 5,743,429 A * | 4/1998 | Morofsky | B65H 3/042 221/253 |
| 5,857,588 A | 1/1999 | Kasper | |
| 5,941,414 A | 8/1999 | Kasper | |
| 6,098,840 A | 8/2000 | Ito et al. | |
| 7,694,873 B1 | 4/2010 | Jones | |
| 7,980,420 B2 * | 7/2011 | Yamamiya | B65H 1/06 221/21 |
| 2005/0211722 A1 * | 9/2005 | Runnels | G07F 11/045 221/259 |
| 2008/0128445 A1 * | 6/2008 | Huang | G07F 9/02 221/7 |
| 2009/0056855 A1 | 3/2009 | Stevens | |
| 2009/0159470 A1 * | 6/2009 | Montakhabi | A61F 5/4556 206/229 |
| 2011/0114660 A1 * | 5/2011 | Johansson | A61F 15/001 221/43 |
| 2012/0286038 A1 | 11/2012 | Wu | |
| 2015/0033460 A1 * | 2/2015 | Mehta | E03D 11/025 4/301 |

OTHER PUBLICATIONS

EP Search Report, dated Apr. 3, 2017, from EP Application No. 17154059.4.

\* cited by examiner

STERILISING AUTOMATIC DISPENSER OF DISPOSABLE DEVICES FOR AID OF FEMALE URINATION IN A STANDING-UP POSITION

The present invention relates to an automatic sterilising dispenser of disposable devices that allow female urination in the standing-up position ("Feminine Urinary Device"—FUD).

The term "Feminine Urinary Device" (FUD) is used to identify devices that allow women to urinate in a standing posture in situations where this is necessary for hygienic reasons, for example when using public bathrooms, or when for reasons of work or sport typically male clothes (trousers, jumpsuits, etc.) are worn.

These devices can be of various shapes, sizes and materials, rigid or flexible, reusable or disposable.

Currently these devices are sold online or in specific stores, in appropriate packaging which ensures the cleanliness thereof.

One of these devices, of the disposable type, was the object of a European patent application EP 594253 A1 in the name of the Applicant, incorporated herein in full by reference.

The device described in EP 594253 A1 consists of a channel element, of substantially conical shape, which comprises a wide end with indentation, which is tilted with respect to the axis of the cone, said wide end acting as a larger base, and an outlet end with oblique opening, opposite to the larger base, which acts as a spout.

This disposable element is made in flexible and foldable material, such as waterproof paper, adequately stiffened, which appears flattened on the two opposite generatrices of the cone in order to be opened in a tubular manner at the time of use.

Since, as is known, the queues in women's toilets are much longer than those in men's toilets, because of the need of having to partially undress and then get dressed again, the advantage of using such "Feminine Urinary Devices" (FUDs) in said toilets accessible to the public is clear. However, at present, this is only possible if one has previously equipped oneself with these devices as there are no automatic dispensers of these devices installed in women's toilets.

The advantage of having available automatic dispensers of sterilized "Feminine Urinary Devices" (FUDs), installable in women's public toilets, preferably automatic dispensers small in size, is clear.

The only possible dispensers on the market for the FUDs would require an outer raping packaging to guarantee at least the cleanliness of a device that is to go in contact with the intimate parts of the feminine body. The problem is that any type of outer raping would cost more than the FUD itself causing the product to rise to a non-affordable price. This is the reason why, at present, there are no automatic dispensers of these devices installed anywhere.

The U.S. Pat. No. 6,098,840 describes an apparatus for dispensing credit cards, phone cards or the like, regular in shape and very slim, which however is not suitable for dispensing products that are not flat and irregularly shaped such as for example FUDs.

The U.S. Pat. No. 5,941,414 describes an apparatus for dispensing slim products with a regular and flat shape, such as tickets, cards and the like, with a pull mechanism which is not suitable for dispensing the FUD in that the latter, as already mentioned, is not a flat product, and does not have a regular shape as a leaf or sheet, essential for handling with this equipment.

The U.S. Pat. No. 5,857,588 also describes an apparatus for dispensing tickets, cards and the like, also of different thickness, which are dispensed through falling through a tilted pan, in which, however, the push mechanism is only suitable for parallelepiped-shaped objects, similarly to previous patents.

The U.S. Pat. No. 5,335,822 also discloses an apparatus similar to that described in U.S. Pat. No. 5,857,588.

SUMMARY OF THE INVENTION

To overcome the problem the Applicant had to conceive and project a completely new dispenser.

In fact, the object of the present invention is to overcome the disadvantages of the prior art by providing a system capable of making available mainly, but not only, in women's toilets accessible to the public, for example in motorway service centres, restaurants, etc., the abovementioned clean and sterilized FUD devices, without overwrapping at a convenient price, in particular those with minimum overall dimensions, such as for example those that appear flattened and without packaging, so as to contain the size of said system.

Another object is to provide such a system that is also able to dispense clean and sterilized yet disposable FUD devices so as to avoid possible contaminations resulting from a possible insufficient cleaning of the reusable device.

Yet another object of the present invention is that of realising such a dispensing device able to supply, at a low price, an FUD of irregular shape and not flat, without packaging but perfectly intact and clean, as close as possible to sterility, avoiding contamination of it during handling.

These and other objects are achieved by the automatic sterilising dispenser in accordance with the invention having the features listed in the appended independent claim.

Advantageous embodiments of the invention are disclosed by the dependent claims.

An object of the present invention relates to an automatic dispenser apt to deliver a disposable "Feminine Urinary Device" (FUD), of flattened shape with an indentation and devoid of a packaging pack, characterised in that it is provided with a system of sanitising and/or sterilising elements, such as for example UV lamps, placed at least at the product outlet slot so as to dispense a disposable FUD device which is sterilised at the time of withdrawal and therefore shortly before use.

This sterilising automatic dispenser is a vending device intended, preferably, to be installed directly in the women's toilets of workplaces, service stations, department stores, cinemas, theatres and other public places where toilets are provided.

Said automatic dispenser can be a wall dispenser or in the form of an automatic or self-service machine, without thereby departing from the scope of the present invention.

Furthermore, this automatic dispenser can dispense the product free of charge or against payment, without thereby departing from the scope of the present invention.

In particular, said automatic dispenser has a system of forward movement and dispensing of FUDs specifically designed to dispense the disposable FUD device with indentation having at least one curved concave portion, distributed in a flattened form and without packaging (loose), in particular described in the European patent application EP 594253 A1 in the name of the Applicant, incorporated herein in full by reference.

As mentioned, such a device aiding female urination in the standing position ("Feminine Urinary Device"—FUD), which is suitable for being dispensed by the present automatic device, consists of a channel element of substantially conical shape, which is able to be flattened on the two opposite generatrices of the cone in order to be dispensed easily and then opened in a tubular manner at the time of use.

Said FUD comprises:
wide end with an indentation with curvilinear profile, said end which is tilted with respect to the axis of the cone, acting as a larger oblique base, and
an oblique outlet end (smaller base defined also as short side), opposite to the larger base and provided with aperture, which serves as a spout.

This disposable element is made in a flexible and foldable material, such as cardboard or waterproof paper, adequately stiffened, which appears flattened on the two opposite generatrices of the cone in order to be easily dispensed individually and then opened in a tubular manner at the time of use.

The system of forward movement and dispensing of FUDs, provides for the forming of a longitudinal slot on the horizontal base on which the FUD to be dispensed rests and the positioning of the specific forward movement and pushing means below said slot so as to allow the direct contact of said FUD with said forward movement means, in particular the direct contact between said indentation and said forward movement and dispensing means, in such a way as to translate horizontally said FUD, resting on said base, towards the dispensing slot so as to make exit therefrom a section of FUD suitable for efficient gripping by the user.

In the present description the terms "product", "product to be dispensed" will be used interchangeably as synonyms of FUD ("Feminine Urinary Device").

It should be noted that the dispensing of a single product without packaging allows the supply of an FUD at an affordable price: in fact, the known devices aiding female urination in a standing position are dispensed with a packaging in which many units of said devices are generally contained, and therefore not suitable for supply in toilets.

Moreover, the absence of packaging, for example of box or package type, makes it impossible to apply the known pusher systems, for example the spiral ones, to the present FUD, also in light of the fact that it has a large curvilinear indentation which is
difficult to grip and push by the known dispensing means.

BRIEF DESCRIPTION OF THE DRAWINGS

Further features of the invention will be made clearer by the following detailed description, referred to one of its purely non-limiting examples, illustrated in the accompanying drawings in which.

DETAILED DESCRIPTION OF THE PREFERRED EMBODIMENTS

Figure 1:
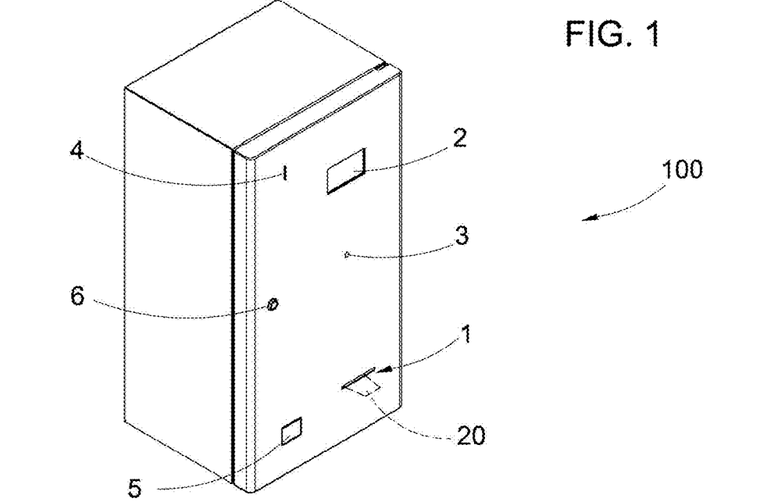
FIG. 1 is a schematic perspective view of the automatic dispenser in accordance with the invention, in its closed configuration in use.

FIG. 1 illustrates a sterilising automatic dispenser of flattened disposable devices as an aid to female urination in the standing position (normally identified with the name "Feminine Urinary Device"—FUD), denoted overall by reference numeral 100.

The automatic dispenser 100 is composed of an outer casing, generally of parallelepiped shape, although this shape is not binding for the purposes of the present invention.

Moreover, also the dimensions of this casing are not binding for the purposes of the present invention, and can be, for example, 780×410×340 (mm), in the case of parallelepiped shape.

As mentioned, the automatic dispenser 100 can adopt, or otherwise, a payment system of the type known in the art, such as a coin system or change giver coin system for payment with coins or other conventional payments systems such as RFID card, banknote reader, etc., without thereby departing from the scope of the present invention.

FIG. 1 shows a coin payment system even if this is not binding for the purposes of the present invention.

On the outer face of the front door of this automatic dispenser 100 the following components are present:
a slot 1 for the output of the dispensed product (FUD indicated as a dotted line in FIG. 1 by reference numeral 20;
a display 2 (optional), possibly of the touch-screen type, to display the cost and/or the operating instructions for the user and/or operations that guide the user during purchase/withdrawal of the product;
at least one button 3, possibly shown on the display 2 if of the touch-screen type, although there may be several buttons depending on the complexity of operation and of management of the various optional components;
a slot 4 for the insertion of coins (optional);
a window 5 for the withdrawal of the change (optional).

In addition, on this outer face a key lock 6 can be provided for closing/opening said front door, even if this lock can be provided on the side wall of the dispenser 100 without thereby departing from the scope of the present invention.

Moreover, on said outer face of said front door a warning light can also be present (optional and therefore not illustrated) to indicate the sold-out product.

Figure 2:
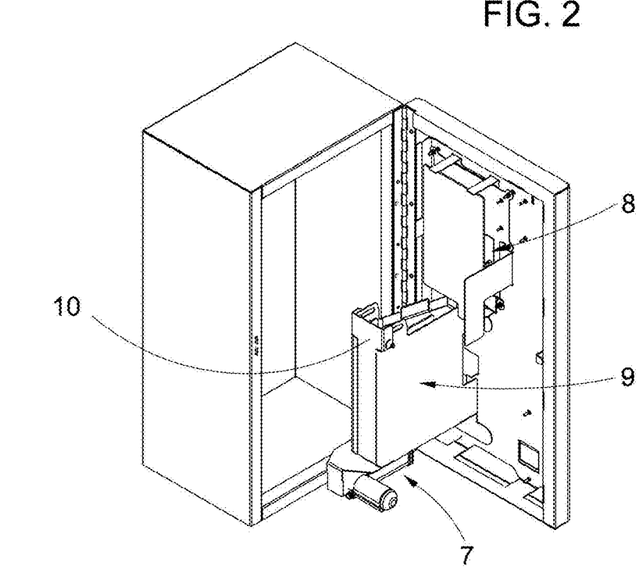
FIG. 2 is a schematic perspective view of the automatic dispenser of FIG. 1 in accordance with the invention, in its open configuration and not in use, which houses a push dispensing and forward movement system according to a first embodiment.
Figure 3:
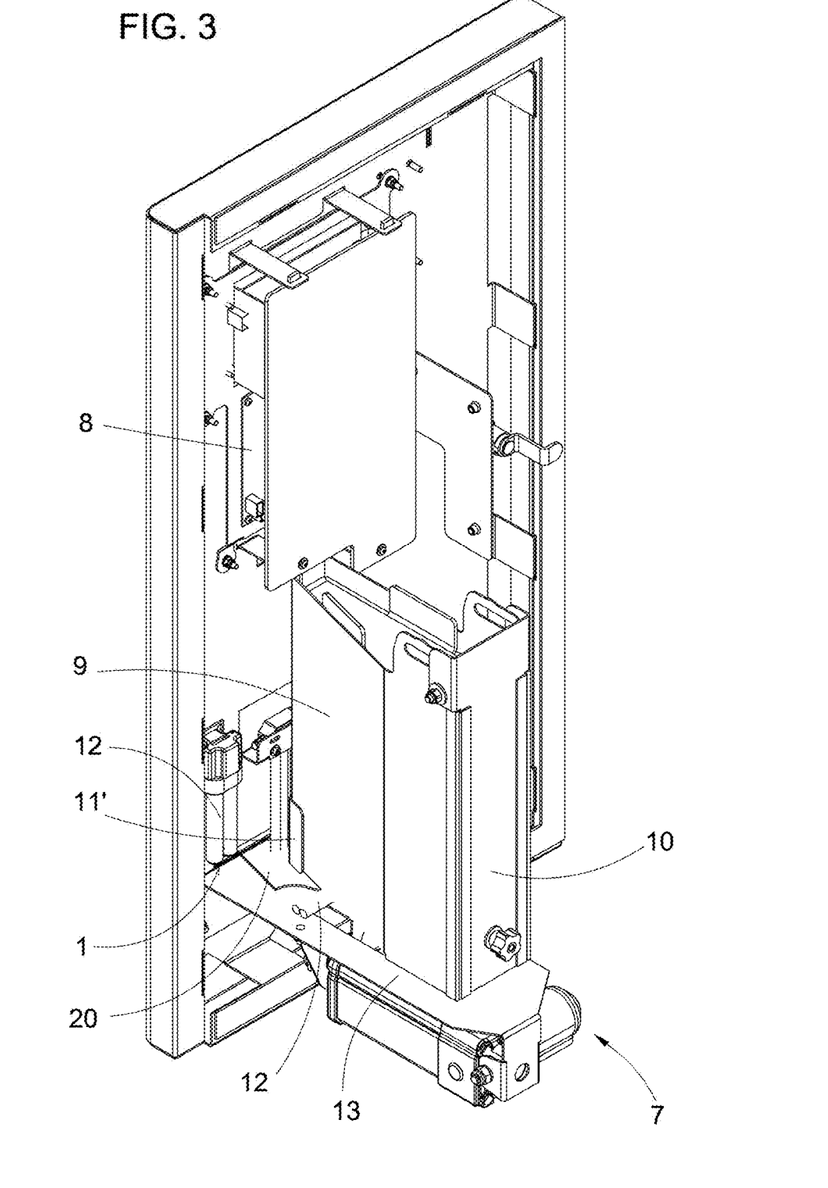
FIG. 3 is an enlarged perspective view of the back of the front door of the dispenser of FIG. 2, in its open configuration and not in use.

As illustrated in FIGS. 2-3, behind the front door, and attached thereto, are the electronic management components 8, for example in the form of electronic card, needed to manage all the components present and the handling/forward movement of the FUD as will be described in detail here below.

Also attached to the back of said front door, a loading container 9 is placed for housing a stack of said flattened disposable FUD devices, preferably the FUD devices described in the European patent application EP 594253 in the name of the Applicant, provided with an indentation.

Said loading container 9 is composed of a metal container, preferably of shape suitable for containing the flattened FUD described in EP594253, generally open on the bottom, which rests on a horizontal plate 13 (FIG. 3) extending as far as the outlet slot 1 so that said plate 13 is aligned with said outlet slot 1, and substantially at the same height of said outlet slot 1.

It is understood that the plate 13 which acts as a lower base for the container 9 may be integral with the container 9 without thereby departing from the scope of the present invention.

Below the support plate 13 or base a push forward movement and dispensing system 7 is placed which will be explained in detail here below.

Said loading container 9 is further provided, preferably, with a closure/opening element 10, in the form of a front door so as to allow a good visual inspection of the state of the stack, avoiding at the same any loading from above.

Furthermore, the container 9 may be provided with a possible sensor for the indication of sold-out product or stock at a minimum (not shown in the drawing).

Having loaded the container 9 with a stack of flattened FUD devices, the insertion is provided on the upper part of the stack of FUDs of a shaped counterweight (not shown in the drawings) to keep compact the stack of the product to be dispensed and maintain the FUD on the bottom of the container 9, always in contact with the plate 13, facilitating the dispensing thereof as will be explained in detail here below.

Also provided on said container 9, on the opposite wall to the door 10, a door 11' adjustable in height thanks to two adjustment screws 11 (FIG. 4) that allow this door 11' to slide vertically along the walls of the container 9 so as to be able to fix appropriately the height of the outlet slot of the FUD 20 from the container 9 depending on the thickness and type of FUD loaded in the container 9.

In the drawings accompanying the present application, the stack of FUDs 20 is placed in the container 9 with the long side 110 of the FUD in contact with the container 9, in turn aligned with the lateral sides of the dispenser 100 so as to make exit the short side 120 (i.e. the smaller oblique base) of the FUD 20 from the slot 1: however, it is understood that the FUD 20 can exit from the long side 110, without thereby departing from the scope of the present invention. It is to be noticed that the exit of the short side 120 from the slot 1 is preferred to avoid any contamination of the long side 110 which is the side intended to be in contact with the body.

Yet another object of the present invention is that of realising such a dispensing device able to supply, at a low price, an FUD of irregular shape and not flat, without packaging but perfectly intact and clean, as close as possible to sterility, avoiding contamination of it during handling.

Behind the front door there are also, in the vicinity of the outlet slot 1 (from which the short side 120 of said single FUD is withdrawn by the user), one or more UV lamps 12 to abate physical and chemical contaminants, viruses, bacteria and moulds, mites, pollens, etc. which are among the main causes of diseases for humans.

Although each of these contaminants is dispersed in a different way, the actual circulation of pollutants in the air means that they can be introduced and multiply.

The use of UV-C has been included among the best practices for protecting objects against contaminations of all kinds.

Ultraviolet rays are electromagnetic waves and are divided according to the wavelengths, expressed in nanometres (nm). Ultraviolet waves with germicidal properties are those comprised between 100 and 280 nm. When bacteria, viruses and other micro-organisms are exposed to UV-C germicidal light with wavelength 253.7 nm, they are inactivated and can no longer pose a threat to human health.

The treatment with UV-C rays is purely physical, and highly ecological, allowing great effectiveness always to be obtained and enabling a considerable reduction in the level of microbial load, maintaining the shelf-life of the products intact, without any contraindication.

The UV-C rays germicidal lamps with direct radiation for the deep disinfection of air and surfaces installed in the present dispenser allow elimination of micro-organisms, including bacteria and moulds, obtaining a 99% reduction.

One or more UV lamps 12' can also be advantageously provided inside the container 9 (FIG. 3) so as to sterilise the entire length of the FUD that is moved towards the outlet slot 1 during dispensing, as will be described subsequently in detail.

Figure 4:
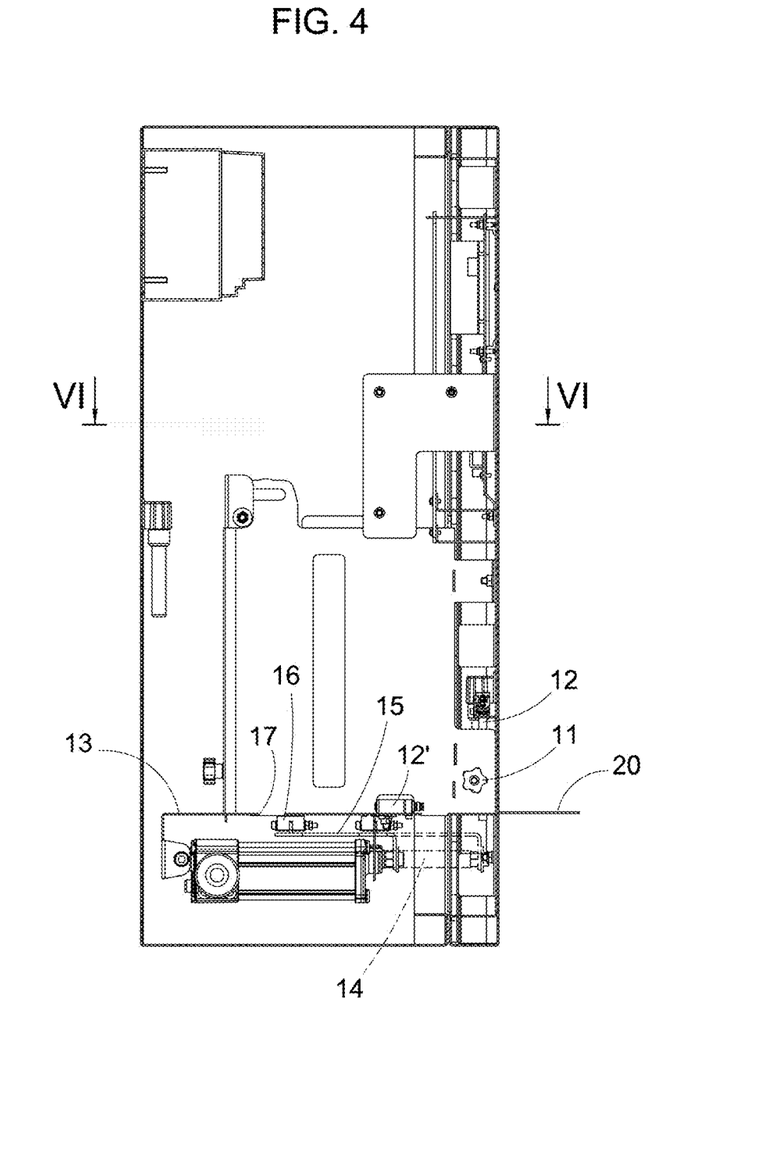
FIG. 4 is a side vertical section of the dispenser of FIG. 1 in accordance with the invention.
Figure 5:
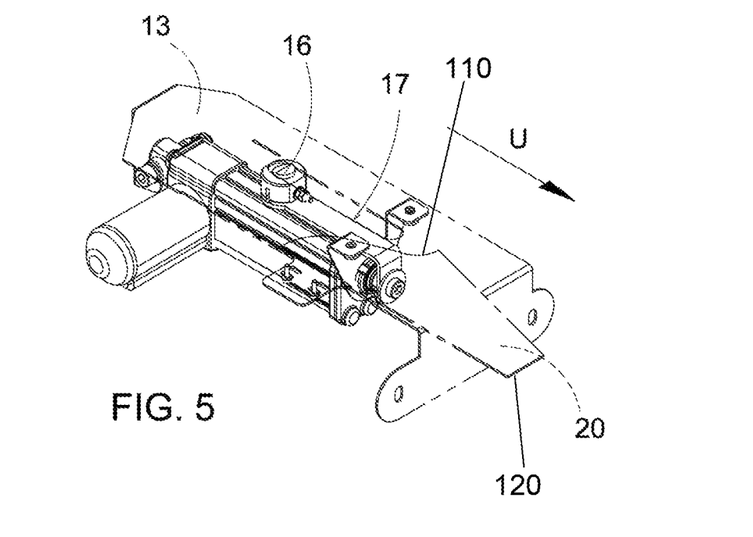
FIG. 5 is an enlarged perspective view of the forward movement and dispensing system of the embodiment illustrated in FIGS. 2-4.
Figure 6:
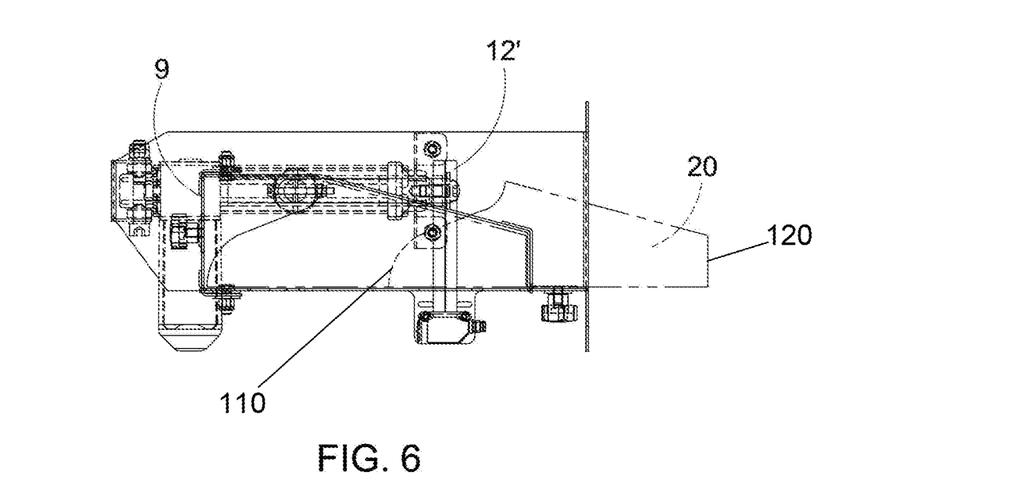
FIG. 6 is a plan and partial view of a horizontal section of the forward movement system taken along line VI-VI of FIG. 4.

Referring to FIGS. 4-6, the embodiment of the pusher system 7 will now be illustrated that enables the product to be dispensed to be moved forwards in the slot 1 for withdrawal provided by means of a direct push on the curved concave portion, otherwise here also referred to as indentation, of said FUD 20 as will be illustrated in detail here below.

In said first embodiment, the pusher system 7, which as mentioned is placed below the plate 13 for support of the loading container 9 (FIG. 3), is an electromechanical linear actuator.

The linear actuator is a mechanism that converts the rotary motion of an electric motor into a linear movement allowing loads to be pushed or pulled.

The present linear actuator 7 is composed of a drive motor with reduction unit, and an actuator stem 14 that moves linearly toward the outlet slot 1 and from said outlet slot 1 towards the interior of the dispenser 100.

Mounted on said actuator stem 14, at the free end, is a rod or arm 15, L-shaped, which in turn has mounted at its free end a mechanical contrast element 16, or ejection block: in this way a linear movement of the stem 14 towards the outlet slot 1 corresponds to a linear movement of the block 16 also towards the outlet slot 1 (indicated by the arrow U in FIG. 5).

Said block 16 slides forwards and backwards inside a longitudinal aperture 17 (FIG. 5) formed in a longitudinal portion of the plate 13 whereon the stack of FUDs 20 contained in the container 9 rests.

The aperture 17, with an elongated shape, is in fact formed at a zone of the plate 13 whereon at least part of the recess (indentation) of the FUD 20 will come to rest.

The length of this longitudinal aperture or slot 17 is such as to provide the FUD 20 with a sufficient movement to make a predefined portion of the FUD 20, preferably the short side 120 thereof, exit from the outlet slot 1.

Said block 16, normally in the form of a small cylinder, has a cylindrical head with a portion thereof which projects partially upwards from the slot 17 with respect to the remaining part of the head (portion not projecting upwards).

Said projecting portion (or protuberance) of said block 16 advantageously has, at its front side (the one frontal to the outlet slot 1), a curved convex profile that is complementary to the concave profile of at least a portion of the indentation of the FUD as shown in FIG. 6: in this way said curved projecting portion of said block 16 can act as a pusher of the FUD 20 when the stem 14 moves forwards in the direction of the arrow indicated by U in FIG. 5, towards the outlet slot 1.

More particularly, when the stem 14 is fully retracted, the protruding part of the block 16 is also in abutment against a part of the inlet of the FUD 20 to be dispensed, which is placed above the slot 17: during the extension stroke of the stem 14 that makes the block 16 move forwards (in the direction of the arrow indicated by U in FIG. 5), the abovementioned protuberance of the block 16 will thus push the FUD 20 forwards in the slot 1 of withdrawal where the user can easily pull it out as shown in FIG. 6.

During the return stroke of the stem 14 (in the opposite direction to the arrow U in FIG. 5), instead, the non-projecting portion of the head of the block 16 will meet the FUD 20 first with respect to the protuberance of the block 16, without acting in any way on said FUD in that not in contact.

Therefore, said projecting portion of said block 16 also acts as end of stroke or stop when said block 16 is retracted as a result of the retraction of the stem 14, once the FUD has been dispensed, since said projecting portion abuts upwards against the rear end of the slot 17 (FIG. 5).

A variant of the pusher can be represented by a system with at least one free rubber-covered wheel illustrated in FIGS. 7-10.

With the exception of this second embodiment of the pusher system, the device 100 has the same elements and features of the previously described dispenser and therefore the same reference numerals will be used here to denote the same components shown in FIGS. 1-6.

Figure 7:
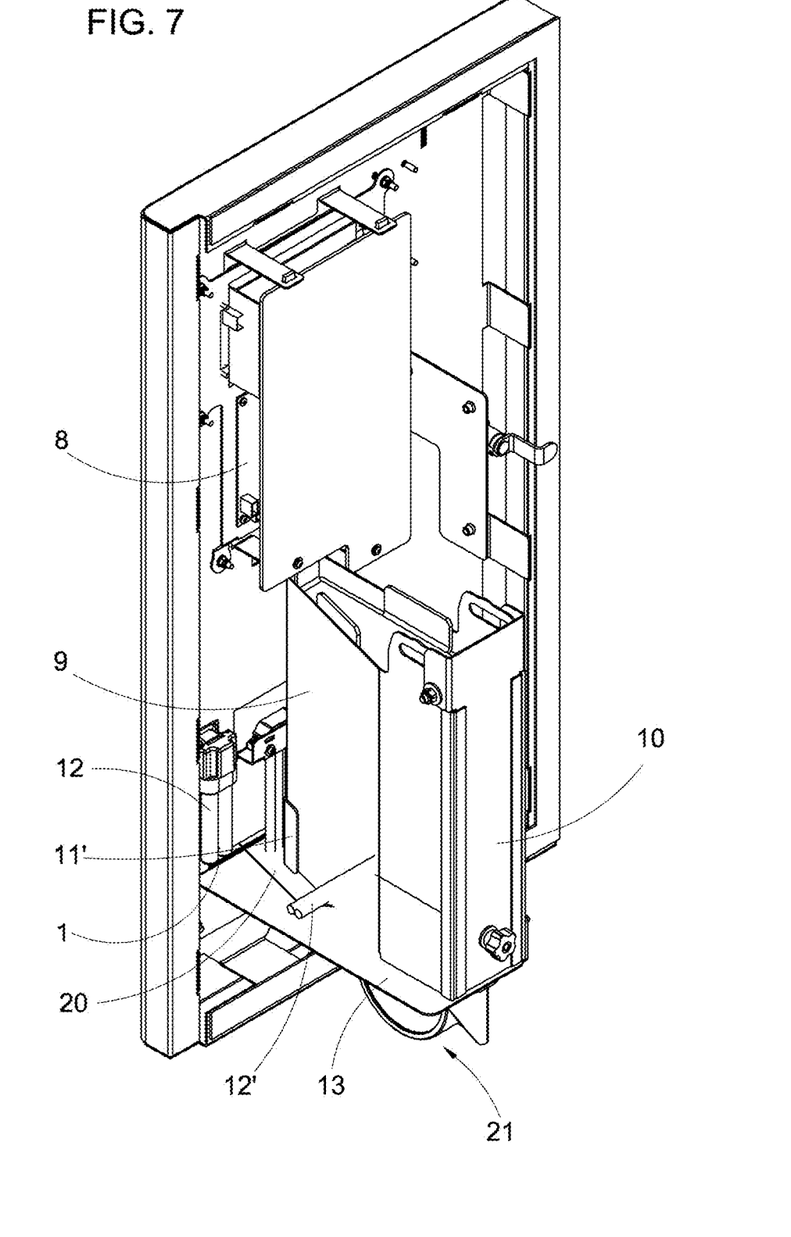
FIG. 7 is an enlarged perspective view of the back of the front door, similar to FIG. 3, of a variant of the forward movement system of the dispenser in accordance with the invention.
Figure 8:
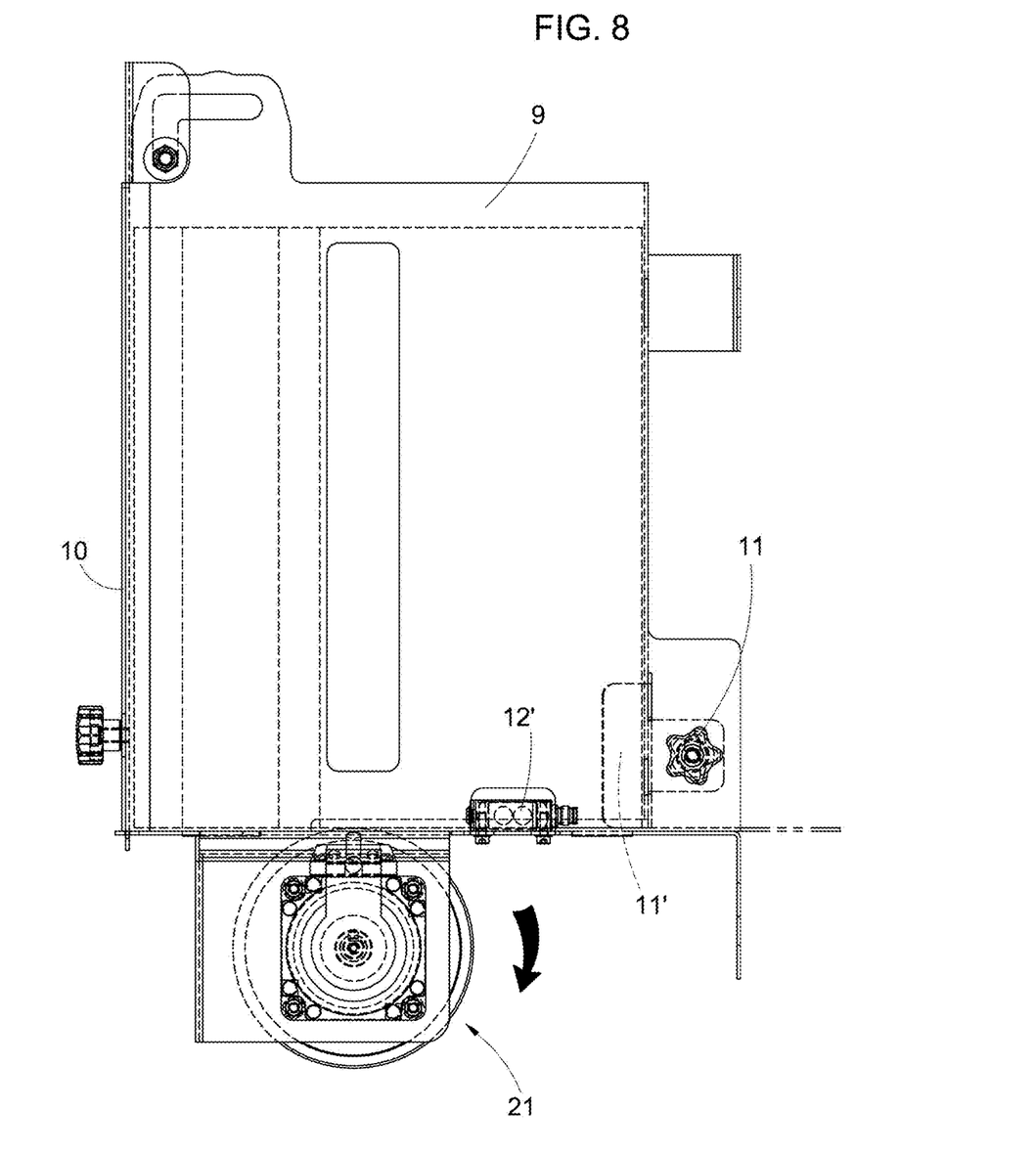
FIG. 8 is a partial side view of FIG. 7 illustrating the container for loading of the product of the dispenser.
Figure 9:
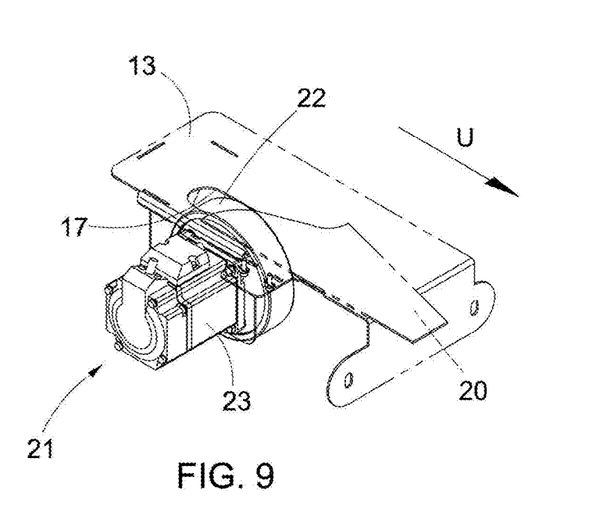
FIG. 9 is an enlarged perspective view of the forward movement system variant shown in FIGS. 7 and 8.
Figure 10:
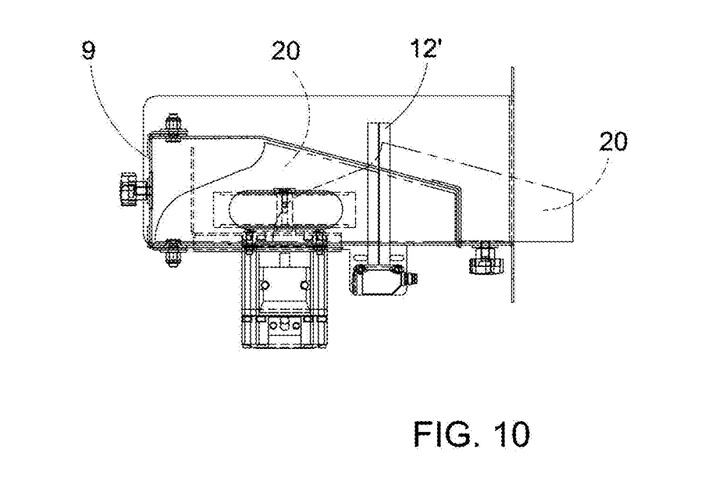
FIG. 10 is a plan view of FIG. 8.

More particularly, behind the front door shown in FIG. 7, there are substantially the same components indicated in FIGS. 1-6: the electronic management components 8, the container 9 for loading of the product to be dispensed, the UV lamps 12 and 12' (inside the container 9), the plate 13 with the longitudinal aperture 17 on which the container 9 rests, with the exception of the pusher system 21 placed below the plate 13 in order to push appropriately the product to be dispensed in the appropriate slot 1 for withdrawal of the same by the user.

The pusher system 21, located below the plate 13 with slot 17, is formed essentially by at least one free rubber-covered wheel 22 attached to a motor or geared motor 23.

Said free rubber-covered wheel 22 which is motorised allows the product to be dispensed to be moved forwards in the slot 1 provided for withdrawal by means of contact with friction of said FUD 20 with said rubber-covered wheel 22.

The slot or longitudinal slit 17 is formed on the plate 13 at the area in which the stack of FUDs 20 rests so as to put into direct contact the surface of the rubber-covered wheel 22 with the surface of the FUD 20.

The length of this slot 17 is at least slightly greater with respect to the diameter of the rubber-covered wheel 22, even if this is not binding for the purposes of the present invention.

The surface of the rubber-covered wheel is preferably uneven so as to create a certain friction with the material that forms the FUD 20.

The wheel-FUD contact is also guaranteed by the counterweight (not shown) placed in the top of the stack of FUDs 20 as mentioned previously.

The dimensions of the wheel 22 are such as to impart to the FUD 20 a predetermined forward movement of such length as to allow the exiting of a portion of FUD sufficient in order to be able to comfortably extract said FUD 20 from the outlet slot 1.

Thanks to the rotary movement of the rubber-covered wheel 22, the FUD 20 is pushed forwards towards the outlet slot 1 for the withdrawal of the same by the user, similarly to what was described previously in relation to the linear actuator 7.

It is understood that other embodiments of pusher means may be provided, for example with two rubber-covered wheels connected one to the other by means of a belt, or using appropriate cams that by performing a semicircular motion dispense the product in a hygienic and convenient position for the user.

As mentioned, it is understood that the FUD product 20 can be dispensed from the long side 110 rather than the short side 120 as shown in the accompanying drawings, without thereby departing from the scope of the present invention.

Irrespective of the type of pusher used, inside the automatic dispenser 100 an electric panel (not shown) is also provided with all the electrical components for the operation of the same.

In relation to the automatic management of the dispensing process, the present automatic dispenser 100 provides, as mentioned, at least one electronic power board with the function of controlling all I/O components of the dispenser 100 and managing the electric actuators or motors, constantly dialoguing with the management software.

However, in the case of a display 2 of the touch-screen type it is preferable to use two electronic cards:
  the first one formed by a power board that deals with the entire control and management of the product dispensing cycles in which the entire sensor part of input (IN) is housed together with the entire power actuation part (OUT);
  the second one formed by a surveillance card for the interface that deals with providing all the interface tools needed by the user using a TFT system with touch screen.

The touch-screen display 2 has the function of interfacing with the user as well as with the personnel carrying out maintenance on the dispenser. This monitor gives all the instructions, including graphic ones, to facilitate the operation of dispensing of the product by the end user.

The various service menus are also given which are useful to the maintenance worker in order to set the parameters of the machine, as well as perform the working tests of the various internal components of the same, download the sales listed and carry out any of the dispenser software updates.

This display has the particular feature of being able to use the following types of connections: Ethernet, modem (optional) and Wi-Fi (optional). These connections allow management and control of the dispenser in an advanced manner, for example by means of specially created Apps that can be installed on smartphones or palmtops which interface directly with the dispenser to obtain sales data, or anything else that might be considered important. The control of the dispenser can also be performed via the Web interface (optional).

If there is a coin system with systems for giving change, it can be composed of an inlet duct, the central part where the store of coins is present and the change giver with its channel bringing the coins into the appropriate space.

The present FUD dispenser is therefore a specific dispensing machine for dispensing individual FUDs without packaging at a very low price, which can be installed in all public women's toilets (railway stations, motorway restaurants, stadiums, theatres, etc.), which is not feasible with any of the dispensing machines existing to date, much less so with the machines described in the prior art patents mentioned above: proof of this is the fact that none of the similar products that are on the market for decades has been able to use this form of sale.

The present invention is not limited to the particular embodiments described previously and illustrated in the accompanying drawings, but instead numerous detail changes may be made thereto within the reach of the person skilled in the art, without thereby departing from the scope of the same invention, as defined in the appended claims.

The invention claimed is:

1. An automatic sterilising dispenser (100) containing single unpackaged flattened disposable devices (20), each one of said flattened disposable devices (20) having a larger oblique base with a curvilinear profile (110) and provided with an indentation, and a smaller oblique base (120), opposite the larger oblique base, said smaller oblique base forming a short side of the flattened disposable device, said sterilising automatic dispenser (100) comprising:
    at least one loading container (9) configured to house a stack of said flattened disposable devices (20) in a substantially compacted form, said container (9) resting on a horizontal base (13);
    an outlet slot (1) from which the short side of one of said flattened disposable devices (20) is withdrawn by a user, one or more UV steriliser elements (12) being located in a vicinity of said outlet slot (1), said outlet slot (1) being aligned with said base (13);
    a dispensing button (3);
    at least one electronic component (8) for dispensing control; and
    means of forward movement and dispensing (7), located beneath said base (13) of said loading container (9) and at a through aperture (17) formed on said base (13) in the form of a horizontal slot,
    wherein said forward movement means (7) are configured to push the one of said flattened disposable devices (20) resting on said base (13) along a length toward said outlet slot (1), by directly pushing upon a curved concave portion of said indentation of the one of said flattened disposable devices (20) in such a way as to cause said short side of the one of said flattened disposable devices to exit from said outlet slot (1) so as to be grippable by the user,
    said forward movement means (7) including a block element (16) that slides along said horizontal slot (17) and has a cylindrical head with a portion thereof partially projecting upwards from said horizontal slot (17) with a rounded convex profile so as to exert a direct push upon the curved portion of said indentation of the one of said flattened disposable devices (20) when said indentation is on said horizontal slot (17) of said base (13).

2. The sterilising automatic dispenser (100) according to claim 1, further comprising:
    a payment system.

3. The sterilising automatic dispenser (100) according to claim 2, further comprising:
    a display (2) configured to present to the user instructions for use of said sterilising automatic dispenser for purchase and withdrawal of the one of said flattened disposable devices (20).

4. The sterilising automatic dispenser (100) according to claim 1, wherein said container (9) provides a sensor connected to a warning light, placed on an outer side of said sterilising automatic dispenser, for indicating sold-out product or minimum stock.

5. The sterilising automatic dispenser (100) according to claim 1, wherein said container (9) includes an opening/closure element (10) for front loading said stack of flattened disposable devices (20).

6. The sterilising automatic dispenser (100) according to claim 1, wherein said container (9) includes one or more UV lamps (12') configured to apply a sterilizing effect on the one of said flattened disposable devices (20) as the one of said flattened disposable devices moves forward towards the outlet slot (1) during the dispensing.

7. The sterilising automatic dispenser (100) according to claim 1, wherein said means (7) of forwarding movement include an electromechanical linear actuator comprised of
    a drive motor with a reduction unit, and
    an actuator stem (14), having an arm (15) at a free end thereof,
    said block element (16) being mounted to a free end of the arm (15).

8. The sterilising automatic dispenser (100) according to claim 1, wherein said outlet slot (1) and said horizontal base (13) are aligned and both placed at a same height.

9. The sterilising automatic dispenser (100) according to claim 1, further comprising at least one from the group consisting of:
    an electrical panel for operation of electrical components; and
    at least one power board (8) for controlling and managing product dispensing cycles.

10. The sterilising automatic dispenser (100) according to claim 2, wherein said container (9) provides a sensor connected to a warning light, placed on an outer side of said sterilising automatic dispenser, for indicating sold-out product or minimum stock.

11. The sterilising automatic dispenser (100) according to claim 3, wherein said container (9) provides a sensor connected to a warning light, placed on an outer side of said sterilising automatic dispenser, for indicating sold-out product or minimum stock.

12. The sterilising automatic dispenser (100) according to claim 2, wherein said container (9) includes an opening/closure element (10) for front loading said stack of flattened disposable devices (20).

13. The sterilising automatic dispenser (100) according to claim 3, wherein said container (9) includes an opening/closure element (10) for front loading said stack of flattened disposable devices (20).

14. The sterilising automatic dispenser (100) according to claim 4, wherein said container (9) includes an opening/closure element (10) for front loading said stack of flattened disposable devices (20).

15. The sterilising automatic dispenser (100) according to claim 2, wherein said container (9) includes one or more UV lamps (12') configured to apply a sterilizing effect on the one of said flattened disposable devices (20) as the one of said flattened disposable devices moves forward towards the outlet slot (1) during the dispensing.

16. The sterilising automatic dispenser (100) according to claim 3, wherein said container (9) includes one or more UV lamps (12') configured to apply a sterilizing effect on the one of said flattened disposable devices (20) as the one of said flattened disposable devices moves forward towards the outlet slot (1) during the dispensing.

17. The sterilising automatic dispenser (100) according to claim 4, wherein said container (9) includes one or more UV lamps (12') configured to apply a sterilizing effect on the one of said flattened disposable devices (20) as the one of said flattened disposable devices moves forward towards the outlet slot (1) during the dispensing.

18. The sterilising automatic dispenser (100) according to claim 5, wherein said container (9) includes one or more UV lamps (12') configured to apply a sterilizing effect on the one of said flattened disposable devices (20) as the one of said flattened disposable devices moves forward towards the outlet slot (1) during the dispensing.

19. The sterilising automatic dispenser (100) according to claim 2, wherein said means (7) of forwarding movement include an electromechanical linear actuator that includes
- a drive motor with a reduction unit, and
- an actuator stem (14), having an arm (15) at a free end thereof,
- said block element (16) being mounted to a free end of the arm (15).

20. The sterilising automatic dispenser (100) according to claim 9, further comprising:
- a surveillance card for interfacing with a touch-screen display (2).

21. The sterilising automatic dispenser (100) according to claim 3, wherein the display (2) is of the touch-screen type.

\* \* \* \* \*